US006960577B2

(12) United States Patent
Tollefson

(10) Patent No.: US 6,960,577 B2
(45) Date of Patent: *Nov. 1, 2005

(54) COMBINATION THERAPY FOR TREATMENT OF REFRACTORY DEPRESSION

(75) Inventor: Gary Dennis Tollefson, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 39 days.

This patent is subject to a terminal disclaimer.

(21) Appl. No.: 10/144,159

(22) Filed: May 10, 2002

(65) Prior Publication Data

US 2003/0212060 A1 Nov. 13, 2003

Related U.S. Application Data

(63) Continuation of application No. 09/700,254, filed as application No. PCT/US99/11276 on May 21, 1999, now abandoned.
(60) Provisional application No. 60/086,444, filed on May 22, 1998.

(51) Int. Cl.[7] ............... A61K 31/137; A61K 31/5513; A61K 31/496

(52) U.S. Cl. ............................. 514/215; 514/649

(58) Field of Search ......................... 514/215, 649

(56) References Cited

U.S. PATENT DOCUMENTS

| 5,500,443 | A | 3/1996 | Lavielle et al. ............ 514/422 |
| 5,977,099 | A | 11/1999 | Nickolson .................. 514/214 |
| 6,130,234 | A | 10/2000 | Bigge et al. ............... 514/322 |
| 6,147,072 | A | 11/2000 | Bymaster et al. ........... 514/220 |

FOREIGN PATENT DOCUMENTS

| EP | 0 830 864 | 9/1996 |
| WO | WO 92/00103 | 6/1990 |
| WO | WO 97/33577 | 3/1996 |
| WO | WO 97/35586 | 3/1996 |
| WO | WO 96/24356 | 8/1996 |
| WO | WO 97/23220 | 7/1997 |
| WO | WO 99/61014 | 5/1998 |
| WO | WO 99/62522 | 5/1998 |

OTHER PUBLICATIONS

Lindsay Devane C. et al: 1998, Guide to psychotropic drug interactions, 1998, pp. 1–39, XP002102289.
Sherman C.: Atypical antipsychotic as adjunt for depression Tx, *Clinical Psychiatry News*, vol. 26, No. 8, 1998, pp. 1–2, XP002115885.
Nidecker A.: Olanzapine may soothe schizophrenic's depression, *Clinical Psychiatry News*, vol. 26, No. 5, 1998, pp. 12–14, XP002115886.
Ananth, Jambur M.D.: Treatment–Resistant Depression, Psychotherapy and Psychosomatics 1998:67, pp. 61–70.
Hungarian Search Report w/Translation.
Sharma V. et al: Treatment of bipolar mixed state with olanzapine,*Journal of Psychiatry and Neuroscience*, vol. 24, No. 1, Jan. 1999, pp. 40–44, XP002116146.
Oyesami O. et al: Hematologic side effects of psychotropics, *Psychosomatics*, vol. 40, No. 5, Sep. 1999, pp. 414–421, XP002116147.
Budavari, S., Ed. The Merck Index—1th Edition, Rahway, New Jersey: Merck & Co., Inc., 1989, p. 653, see entry No. 4112 entitled "Fluoxetine".
97–45747, Miller D D. et al: Effect of antipsychotics on regional cerebral blood flow measured with positron emission tomography, abstract, *Neuropsychopharmacology*, 17(4), 230–240, 1997.
98–170902, Weisler R. H. et al: Adjunctive use of olanzapine in mood disorders: five case reports, abstract,*Annals of Clinical Psychiatry*, 9(4), 259–262, Dec. 1997.
97–44995, Devane C. L. et al: Fluvoxamine–induced theophylline toxicity, abstract, *American Journal of Psychiatry*, 154(9), 1317–1318, 1997.
Andrew A. Nicrenberg, M.D.; Rachel D. McColl, BA.; Management Options for Refractory Depression; *The American Journal of Medicine*, vol. 101 (Suppl. 6A). Dec. 30, 1996, pp. 455–525.
Maurizio Fava, et al.; Pharmacologic Strategies for Treatment–Resistant Major Depression; *Challenges in Clinical Practice: Pharmacologic and Psychosocial Strategies, New York, NY: Guilford Press*, 1996, pp. 3–30.
Michael E. Thase, M.D.; A. John Rush, M.D.; Treatment–Resistant Depression: *Psychopharmacology: The Fourth Generation of Progress, Raven Press Ltd., New York*, 1995, pp. 1081–1097.
Michael E. Thase, M.D.; A. John Rush, M.D.; When at First You Don't Succeed: Sequential Strategies for Antidepressant Nonrespondres; *J. Clin. Psychiatry*, vol. 58 (suppl 13), 1997, pp. 23–29.
Robert B. Ostroff, M.D.; J. Craig Nelson, M.D.; Risperidone Augmentation of Selective Serotonin Reuptake Inhibitors in Major Depression; *J. Clin. Psychiatry*, 60:4, Apr. 1999, pp. 256–259.
Maurizio Fava, M.D.; New Approaches to the Treatment of Refractory Depression; *J. Clin. Psychiatry 2000:61* (suppl 1), pp. 26–32.

(Continued)

*Primary Examiner*—Phyllis G. Spivack
(74) *Attorney, Agent, or Firm*—Nelsen L. Lentz; Arleen Palmberg

(57) ABSTRACT

Methods for treating a patient suffering from or susceptible to treatment resistant major depression comprising administering olanzapine and fluoxetine are disclosed.

4 Claims, No Drawings

OTHER PUBLICATIONS

Shelton, R.; Tollefson; M. Tohen; W. Buras; K.S. Gannon; S. Stahl; The Study of Olanzapine Plus Fluoxetine in Treatment-Resistant Major Depressive Disorder Without Psychotic Features; 38$^{th}$ New Clinical Drug Evaluation Unit (NCDEU) Annual Meeting; Boca Raton, Florida; Jun. 10–13, 1998.

J. Craig Nelson, M.D.; Augmentation Strategies with Serotonergic–Noradrenergic Combinations: *J. Clin. Psychiatry 1998:59* (suppl 5), pp. 65–68.

Nelson, J.C.; The use of antipsychotic drugs in treatment of depression; PMA Publishing, Eds: Zohar J., Belmaker R.H., pp. 131–146, 1987.

Zhang Wei; M.D. et al.; Synergistic Effects of Olanzapine and Other Antipsychotic Agents in Combination with Fluoxetine on Norepinephrine and Dopamine Release in Rat Prefrontal Cortex; *Neuropsychopharmacology*, vol. 23, No. 3, pp. 250–262, 2000.

Guscott, Richard et al.: The Clinical Meaning of Refractory Depression: A Review for the Clinician, Am J. Psychiatry 148:6, Jun. 1991, pp. 695–704.

Thase, Michael et al.: Tricyclics and New Antidepressant Medications: Treatment Options for Treatment-Resistant Depressions, Depression 2:152–168 (1994/1995).

Miller, Del D. et al.: Effect of Antipsychotics on Regional Cerebral Blood Flow Measured with Positron Emission Tomography, Neuropsychopharmacology 1997, vol. 17, No. 4, pp. 230–240.

Bakishi, David, M.D.: Fluoxetine Potentiation by Buspirone: Three Case Histories, Can. J. Psychiatry, vol. 36, Dec. 1991, pp. 749–750.

Ananth, Jambur M.D.: Treatment-Resistant Depression, Psychotherapy and Psychosomatics 1998:67, pp. 61–70.

COMBINATION THERAPY FOR TREATMENT OF REFRACTORY DEPRESSION

This is a continuation application of U. S. application Ser. No. 09/700,254, filed Nov. 9, 2000 abandoned which is a 371 of PCT/US99/11276 filed May 21, 1999 which claims priority to U.S. Provisional Application No. 60/086,444 filed May 22, 1998.

The present invention belongs to the fields of pharmacology, medicine and medicinal chemistry, and provides methods and compositions for treating refractory depression or partial responders.

Depression in its many variations has recently become much more visible to the general public than it has previously been. It is now recognized as an extremely damaging disorder, and one that afflicts a surprisingly large fraction of the population. Suicide is the most extreme symptom of depression, but millions of people, not quite so drastically afflicted, live in misery and partial or complete uselessness, and afflict their families as well by their affliction. The introduction of fluoxetine, a serotonin reuptake inhibitor (SRI), was a breakthrough in the treatment of depression, and depressives are now much more likely to be diagnosed and treated than they were only a decade ago.

Depression is often associated with other diseases and conditions, or caused by such other conditions. For example, it is associated with Parkinson's disease; with HIV infection; with Alzheimer's disease; and with abuse of anabolic steroids. Depression may also be associated with abuse of any substance, or may be associated with behavioral problems resulting from or occurring in combination with head injuries, mental retardation or stroke.

Despite the breakthrough nature of selective serotonin reuptake inhibitors in the treatment of depression, a number of patients suffering from major depression do not respond, or respond only partially to treatment with SRIs or other traditional modes of treating depression, including the older tricyclics. The present invention addresses this by offering methods of treating patients suffering from refractory depression, or partially responding. Additionally, as there is frequently a significant period of time before treatment with SRIs can have a therapeutic effect, this invention provides a therapeutic benefit in providing methods of treating depressing by a more rapid onset, while attenuating adverse events frequently associated with conventional antidepressant medication.

The invention provides a method for treating a patient suffering from or susceptible to refractory depression, comprising administering to said patient an effective amount of a first component which is an atypical antipsychotic, in combination with an effective amount of a second component which is a serotonin reuptake inhibitor.

In addition, this invention provides a method for treating a patient partially responding to treatment for depression, which comprises administering to said patient an effective amount of a first component which is an atypical antipsychotic, in combination with an effective amount of a second component which is a serotonin reuptake inhibitor.

This invention provides, further, a method for attenuating adverse events associated with treating a patient suffering from or susceptible to refractory depression which comprises administering to said patient an effective amount of a first component which is an atypical antipsychotic, in combination with an effective amount of a second component which is a serotonin reuptake inhibitor.

This invention also provides a method of providing rapid onset treatment of depression to a patient which comprises administering to said patient an effective amount of a first component which is an atypical antipsychotic, in combination with an effective amount of a second component which is a serotonin reuptake inhibitor.

The invention also provides a pharmaceutical composition which comprises a first component which is an atypical antipsychotic, and a second component which is a serotonin reuptake inhibitor, the two compounds being present in an amount effective in the treatment of depression refractory to traditional pharmaceutical intervention.

By "partial response" is meant an improvement of less than 50% on the HAMD-21 or Montgomery-Asberg Depression Rating Scale, preferably from about 1% to about 49%, more preferably from about 10% to about 49%, most preferably from about 15% to about 49%.

The term "attenuating" means decreasing the number, severity or frequency of side effects or adverse events associated with treatment of depression with conventional antidepressant medication, including tucylics and SSRIs, when such products are used at dosages that yield beneficial effects on the symptoms of the disease.

The term "activation" means agitation.

The term "sexual dysfunction" means a disturbance or variation in the pattern of human sexual response (excitement phase, plateau phase, orgasmic phase and resolution phase), Masters et al., *Human Sexual Response*, Little Brown and Company, Boston, 1966 and *Human Sexual Inadequacy*, Little Brown and Company, Boston, 1970. Included are disorders related to the erectile response in male mammals and the sexual desire and sexual (both arousal and orgasmic) reflexes in male or female mammals such as decreased libido, erectile dysfunction, retarded ejaculation and anorgasmy.

In this document, all temperatures are described in degrees Celsius, and all amounts, ratios of amounts and concentrations are described in weight units unless otherwise stated.

The Compounds

In the general expressions of the present invention, the first component is a compound which acts as an atypical antipsychotic. The essential feature of an atypical antipsychotic is less acute extrapyramidal symptoms, especially dystonias, associated with therapy as compared to a typical antipsychotic such as haloperidol. Clozapine, the prototypical atypical antipsychotic, differs from the typical antipsychotics with the following characteristics: (1) greater efficacy in the treatment of overall psychopathology in patients with schizophrenia nonresponsive to typical antipsychotics; (2) greater efficacy in the treatment of negative symptoms of schizophrenia; and (3) less frequent and quantitatively smaller increases in serum prolactin concentrations associated with therapy (Beasley, et al., *Neuropsychopharmacology*, 14(2), 111–123, (1996)). Atypical antipsychotics include, but are not limited to:

Olanzapine, 2-methyl-4-(4-methyl-1-piperazinyl)-10H-thieno[2,3-b][1,5]benzodiazepine, is a known compound and is described in U.S. Pat. No. 5,229,382 as being useful for the treatment of schizophrenia, schizophreniform disorder, acute mania, mild anxiety states, and psychosis. U.S. Pat. No. 5,229,382 is herein incorporated by reference in its entirety;

Clozapine, 8-chloro-11-(4-methyl-1-piperazinyl)-5H-dibenzo[b,e][1,4]diazepine, is described in U.S. Pat. No. 3,539,573, which is herein incorporated by reference in its entirety. Clinical efficacy in the treatment of schizophrenia is described (Hanes, et al., *Psychopharmacol. Bull.*, 24, 62 (1988));

Risperidone, 3-[2-[4-(6-fluoro-1,2-benzisoxazol-3-yl) piperidino]ethyl]-2-methyl-6, 7,8,9-tetrahydro-4H-pyrido [1,2-a]pyrimidin-4-one, and its use in the treatment of psychotic diseases are described in U.S. Pat. No. 4,804,663, which is herein incorporated by reference in its entirety;

Sertindole, 1-[2-[4-[5-chloro-1-(4-fluorophenyl)-1H-indol-3-yl ]-1-piperidinyl]ethyl]imidazolidin-2-one, is described in U.S. Pat. No. 4,710,500. Its use in the treatment of schizophrenia is described in U.S. Pat. Nos. 5,112,838 and 5,238,945. U.S. Pat. Nos. 4,710,500; 5,112,838; and 5,238,945 are herein incorporated by reference in their entirety;

Quetiapine, 5-[2-(4-dibenzo[b,f][1,4]thiazepin-11-yl-1-piperazinyl)ethoxy]ethanol, and its activity in assays which demonstrate utility in the treatment of schizophrenia are described in U.S. Pat. No. 4,879,288, which is herein incorporated by reference in its entirety. Quetiapine is typically administered as its (E)-2-butenedioate (2:1) salt; and Ziprasidone, 5-[2-[4-(1,2-benzoisothiazol-3-yl)-1-piperazinyl]ethyl]-6-chloro-1,3-dihydro-2H-indol-2-one, is typically administered as the hydrochloride monohydrate. The compound is described in U.S. Pat. Nos. 4,831,031 and 5,312,925. Its activity in assays which demonstrate utility in the treatment of schizophrenia are described in U.S. Pat. No. 4,831,031. U.S. Pat. Nos. 4,831,031 and 5,312,925 are herein incorporated by reference in their entirety.

Similarly, when the invention is regarded in its broadest sense, the second component compound is a compound which functions as a serotonin reuptake inhibitor. The measurement of a compound's activity in that utility is now a standard pharmacological assay. Wong, et al., *Neuropsychopharmacology* 8, 337–344 (1993). Many compounds, including those discussed at length above, have such activity, and no doubt many more will be identified in the future. In the practice of the present invention, it is intended to include reuptake inhibitors which show 50% effective concentrations of about 1000 nM or less, in the protocol described by Wong supra. Serotonin reuptake inhibitors include, but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761, 501. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology* 24, 1211–19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., *Eur. J. Pharmacol.* 41, 153 (1977), and reports of its clinical effectiveness in depression may be found in Dufour et al., *Int. Clin. Psychopharmacol.* 2, 225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., *Brit. J. Pharmacol.* 60, 505 (1977); and De Wilde et al., *J. Affective Disord.* 4, 249 (1982); and Benfield et al., *Drugs* 32, 313 (1986);

Paroxetine, trans-(−)-3-[(1,3-benzodioxol-5-yloxy) methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan et al., *Brit. J. Clin. Pharmacol.* 19, 705 (1985); Laursen et al., *Acta Psychiat. Scand.* 71, 249 (1985); and Battegay et al., *Neuropsychobiology* 13, 31 (1985); and Sertraline, (1S-cis)-4-(3,4-dichlorophenyl)-1,2,3,4-tetrahydro-N-methyl-1-naphthylamine hydrochloride, is a serotonin reuptake inhibitor which is marketed as an antidepressant. It is disclosed by U.S. Pat. No. 4,536,518.

All of the U.S. patents which have been mentioned above in connection with compounds used in the present invention are incorporated herein by reference.

It will be understood that while the use of a single atypical antipsychotic as a first component compound is preferred, combinations of two or more atypical antipsychotics may be used as a first component if necessary or desired. Similarly, while the use of a single serotonin reuptake inhibitor as a second component compound is preferred, combinations of two or more serotonin reuptake inhibitors may be used as a second component if necessary or desired.

While all combinations of first and second component compounds are useful and valuable, certain combinations are particularly valued and are preferred, as follows:

olanzapine/fluoxetine
olanzapine/venlafaxine
olanzapine/citralopram
olanzapine/fluvoxamnine
olanzapine/paroxetine
olanzapine/sertraline
olanzapine/milnacipran
olanzapine/duloxetine
clozapine/fluoxetine
risperidone/fluoxetine
sertindole/fluoxetine
quetiapine/fluoxetine
ziprasidone/fluoxetine In general, combinations and methods of treatment using olanzapine as the first component are preferred. Furthermore, combinations and methods of treatment using fluoxetine as the second component are preferred. Especially preferred are combinations and methods of treatment using olanzapine as the first component and fluoxetine as the second component.

It is especially preferred that when the first component is olanzapine, it will be the Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper $K_a$ radiation source of wavelength, 1=1.541 Å.

It is further preferred that the Form II olanzapine polymorph will be administered as the substantially pure Form II olanzapine polymorph.

As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

The polymorph obtainable by the process taught in the '382 patent will be designated as Form I and has a typical x-ray powder diffraction pattern substantially as follows, obtained using a Siemens D5000 x-ray powder diffractometer, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and $I/I_1$ represents the typical relative intensities:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |

-continued

| d | I/I$_1$ |
|---|---|
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_a$ of wavelength 1=1.541 Å. The interplanar spacings in the column marked "d" are in Angstroms. The typical relative intensities are in the column marked "I/I$_1$".

Though Form II olanzapine is preferred it will be understood that as used herein, the term "olanzapine" embraces all solvate and polymorphic forms unless specifically indicated.

PREPARATION 1

Technical Grade Olanzapine

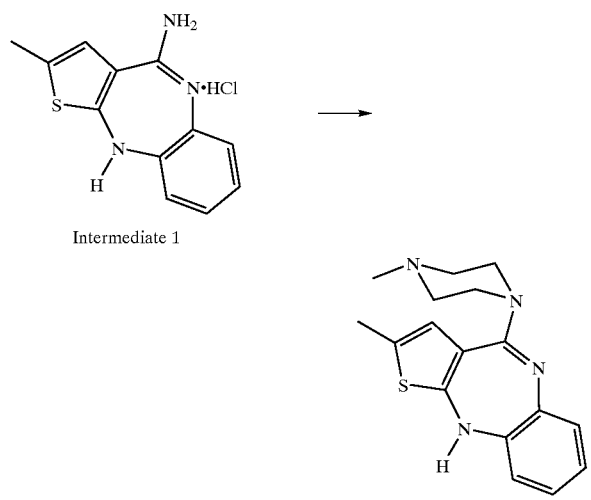

Intermediate 1

In a suitable three neck flask the following was added:

| Dimethylsulfoxide (analytical) | 6 volumes |
|---|---|
| Intermediate 1 | 75 g |
| N-Methylpiperazine (reagent) | 6 equivalents |

Intermediate 1 can be prepared using methods known to the skilled artisan. For example, the preparation of the Intermediate 1 is taught in the above-referenced '382 patent.

A sub-surface nitrogen sparge line was added to remove the ammonia formed during the reaction. The reaction was heated to 120° C. and maintained at that temperature throughout the duration of the reaction. The reactions were followed by HPLC until=5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

PREPARATION 2

Form II Olanzapine Polymorph

A 270 g sample of technical grade 2-methyl-4-(4-methyl-1-piperazinyl)-10H-thieno[2,3-b][1,5]benzodiazepine was suspended in anhydrous ethyl acetate (2.7 L). The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency $\geq$97%, total related substances <0.5% and an isolated yield of >73%.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Many of the compounds used in this invention are amines, and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

Administration

The dosages of the drugs used in the present invention must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, can and will be provided here. Dosage guidelines for some of the drugs will first be given separately; in order to create a guideline for any desired combination, one would choose the guidelines for each of the component drugs.

Olanzapine: from about 0.25 to 100 mg, once/day; preferred, from 1 to 30 mg, once/day and most preferably 1 to 25 mg once/day;

Clozapine: from about 12.5 to 900 mg daily; preferred, from about 150 to 450 mg daily;

Risperidone: from about 0.25 to 16 mg daily; preferred from about 2–8 mg daily;

Sertindole: from about 0.0001 to 1.0 mg/kg daily;

Quetiapine: from about 1.0 to 40 mg/kg given once daily or in divided doses;

Ziprasidone: from about 5 to 500 mg daily; preferred from about 50 to 100 mg daily;

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 160 mg once/day (or up to 80 mg twice daily); preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 20 to about 50 mg once/day; preferred, from about 20 to about 30 mg once/day.

Sertraline: from about 20 to about 500 mg once/day; preferred, from about 50 to about 200 mg once/day;

In more general terms, one would create a combination of the present invention by choosing a dosage of first and second component compounds according to the spirit of the above guideline.

Preferred ratios of olanzapine: fluoxetine by weight include:

1/5
6/25
12.5/25
25/50
17.5/50
25/75

The adjunctive therapy of the present invention is carried out by administering a first component together with the second component in any manner which provides effective levels of the compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the others may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

The adjunctive combination may be administered as a single pharmaceutical composition, and so pharmaceutical compositions incorporating both compounds are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of all compounds, or may contain a fraction of the daily doses, such as one-third of the doses. Alternatively, each dosage unit may contain the entire dose of one of the compounds, and a fraction of the dose of the other compounds. In such case, the patient would daily take one of the combination dosage units, and one or more units containing only the other compounds. The amounts of each drug to be contained in each dosage unit depends on the identity of the drugs chosen for the therapy, and other factors such as the indication for which the adjunctive therapy is being given.

The inert ingredients and manner of formulation of the adjunctive pharmaceutical compositions are conventional, except for the presence of the combination of the present invention. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations do not depend on the nature of the composition, so the compositions are chosen and formulated solely for convenience and economy. Any of the combinations may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. It is preferred to formulate duloxetine and duloxetine-containing combinations as enteric compositions, and even more preferred to formulate them as enteric pellets.

A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. This enteric formulation is described in U.S. Pat. No. 5,508,276, herein incorporated by reference in its entirety.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following typical formulae are provided for the interest and information of the pharmaceutical scientist.

FORMULATION 1

Hard gelatin capsules are prepared using the following ingredients:

|  | Quantity (mg/capsule) |
| --- | --- |
| Olanzapine | 25 mg |
| Fluoxetine, racemic, hydrochloride | 20 |
| Starch, dried | 150 |
| Magnesium stearate | 10 |
| Total | 210 mg |

FORMULATION 2

A tablet is prepared using the ingredients below:

|  | Quantity (mg/capsule) |
| --- | --- |
| Olanzapine | 10 |
| Fluoxetine, racemic, hydrochloride | 10 |
| Cellulose, microcrystalline | 275 |
| Silicon dioxide, fumed | 10 |
| Stearic acid | 5 |
| Total | 310 mg |

The components are blended and compressed to form tablets each weighing 465 mg.

FORMULATION 3

An aerosol solution is prepared containing the following components:

|  | Weight |
| --- | --- |
| Risperidone | 5 mg |
| (+)-Duloxetine, hydrochloride | 10 |
| Ethanol | 25.75 |
| Propellant 22 (Chlorodifluoromethane) | 60.00 |
| Total | 100.75 mg |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 80 mg of active ingredient, are made as follows:

| | |
|---|---:|
| Sertindole | 60 mg |
| (+)-Duloxetine, hydrochloride | 20 mg |
| Starch | 30 mg |
| Microcrystalline cellulose | 20 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 140 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 170 mg.

FORMULATION 5

Capsules, each containing 130 mg of active ingredient, are made as follows:

| | |
|---|---:|
| Quetiapine | 70 mg |
| Fluoxetine, racemic, hydrochloride | 30 mg |
| Starch | 39 mg |
| Microcrystalline cellulose | 39 mg |
| Magnesium stearate | 2 mg |
| Total | 180 mg |

The active ingredient, cellulose, search, and magnesium stearate are blended, passed through a No. 45 mesh U.S. sieve, and filled into hard gelatin capsules in 250 mg quantities.

FORMULATION 6

Suppositories, each containing 45 mg of active ingredient, are made as follows:

| | |
|---|---:|
| Ziprasidone | 75 mg |
| (+)-Duloxetine, hydrochloride | 5 mg |
| Saturated fatty acid glycerides | 2,000 mg |
| Total | 2,080 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 70 mg of active ingredient per 5 ml dose, are made as follows:

| | |
|---|---:|
| Olanzapine | 20 mg |
| Sertraline | 100 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---:|
| Olanzapine | 20 mg |
| Paroxetine | 25 mg |
| Isotonic saline | 1,000 ml |

Benefit of the Invention

The present invention provides the advantage of treatment of partial responding or refractory depression with the atypical antipsychotics without the concomitant weight gain typically observed with such treatment, conferring a marked and unexpected benefit on the patient. The present invention furthermore provides a potentiation of the increase in the concentration of dopamine and/or norepinephrine observed as an effect of administration of a first component compound, by administration of a second component compound.

Moreover, the release of DA in the prefrontal cortex, either coupled with the antagonism of $5\text{-}HT_2$ and/or $5\text{-}HT_3$ receptors, would be expected to attenuate the disturbances in sexual function commonly associated with antidepressants such as the SSRIs. In addition, common SSRI-associated side effects such as nausea, vomiting, diarrhea, insomnia, weight change, headache, and or activation would be expected to be reduced in frequency/intensity based on the pharmacology of this novel combination.

Microdialysis Assays of Monoamines

Sprague-Dawley rats (Harlan or Charles River) weighing 270–300 grams are surgically implanted with microdialysis probes under chloral hydrate/pentobarbital anesthesia (170 and 36 mg/kg i.p. in 30% propylene glycol, 14% ethanol) (Perry and Fuller, Effect of fluoxetine on serotonin and dopamine concentration in rat hypothalamus after administration of fluoxetine plus L-5-hydroxytryptophan, Life Sci., 50, 1683–90 (1992)). A David Kopf stereotaxic instrument is used to implant the probe unilaterally in the hypothalamus at coordinates rostral −1.5 mm, lateral −1.3 mm, and ventral −9.0 mm (Paxinos and Watson, 1986). After a 48 hour recovery period, rats are placed in a large plastic bowl with a mounted liquid swivel system (CMA/120 system for freely moving animals, Bioanalytical Systems, West Lafayette, Ind.). Filtered artificial cerebrospinal fluid (CSF) (150 mM NaCl, 3.0 mM KCl, 1.7 mM $CaCl_2$, and 0.9 mM $MgCl_2$) is perfused through the probe at a rate of 1.0 ml/min. The output dialysate line is fitted to a tenport HPLC valve with a 20 ml loop. At the end of each 30 minute sampling period, dialysate collected in the loop is injected on an analytical column (Spherisorb 3 m ODS2, 2×150 mm, Keystone Scientific).

The method used to measure monoamines is as described by Perry and Fuller (1992). Briefly, dialysate collected in the 20 ml loop is assayed for 5-HT, NE and DA. The 20 ml injection goes onto the column with a mobile phase which resolves NE, DA, and 5-HT: 75 mM potassium acetate, 0.5 mM ethylenediaminetetraacetic acid, 1.4 mM sodium octanesulfonic acid and 8% methanol, pH 4.9. The mobile phase for the amine column is delivered with a flow programmable pump at an initial flow rate of 0.2 ml/min increasing to 0.3 ml/min at 5 min then decreasing back to 0.2 ml/min at 26 min with a total run time of 30 min. Flow programming is used to elute the 5-HT within a 25 min time period. The electrochemical detector (EG&G, Model 400) for the amine column is set at a potential of 400 mV and a sensitivity of 0.2 nA/V. Basal levels are measured for at least 90 minutes prior to drug administration. The drugs are prepared in filtered deionized water (volume 0.25–0.3 ml) for administration at the desired doses.

Clinical Trials

The efficacy of the methods of the present invention in treating refractory depression or providing a more rapid onset of treatment of depression was shown in clinical trials. In one such study, an 8-week, double blind trial, 28 patients diagnosed with treatment-resistant major depression were randomized to one of three treatment arms: (1) fluoxetine (20–60 mg/day) and placebo; (2) olanzapine (5–20 mg/day) and placebo; or (3) fluoxetine plus olanzapine (20–60 mg/day and 5–20 mg/day, respectively). The efficacy of the treatment was monitored using the HAMD-21 (Hamilton M. Journal of Neurology, Neurosurgery & Psychiatry. 1960.23:56–62, and Hamilton M. Development of a rating scale for primary depressive illness. British Journal of Social and Clinical Psychology. 1967;6:278–296); Montgomery-Asberg Depression Rating Scale (MADRS) (Montgomery S A, Asberg M. A new depression scale designed to be sensitive to change. British Journal of Psychiatry. 1979;134:382–389); and the Clinical Global Impression (CGI)—Severity of Depression rating scale (Guy, W. ECDEU Assessment Manual for Psychopharmacology. Revised ed. US Dept. of Health, Education and Welfare, Bethesda, Md. 1976.) The olanzapine plus fluoxetine group experienced a greater improvement on both the HAMD-21 and MADRS total scores than either of the monotherapy groups. Superior rates of response (i.e., 50% or greater improvement from baseline) were also seen with this combination. Similar results were obtained using the CGI scale.

The antidepressant effect of olanzapine plus fluoxetine was evident within seven days of beginning the therapy. This is significantly earlier than is generally seen with a monotherapy using a serotonin uptake inhibitor alone, with no evidence of significant adverse interaction between the antipsychotic and the serotonin reuptake inhibitor.

I claim:

1. A method for treating a patient suffering from or susceptible to treatment resistant major depression, comprising administering to said patient an effective amount of a first component which is olanzapine or a pharmaceutically acceptable salt thereof, in combination with an effective amount of a second component which is fluoxetine, or a phannaceutically acceptable salt thereof.

2. A method according to claim 1 where the administration of the compounds is oral.

3. A method for treating a patient suffering from or susceptible to treatment resistant major depression, comprising administering to said patient an effective amount of a first component which is olanzapine, in combination with an effective amount of a second component which is fluoxetine.

4. A method for treating a patient suffering from or susceptible to treatment resistant major depression, comprising administering to said patient an effective amount of a first component which is olanzapine in combination with an effective amount of a second component which is fluoxetine hydrochloride.

* * * * *